United States Patent
Jonsson et al.

(10) Patent No.: US 9,347,958 B2
(45) Date of Patent: May 24, 2016

(54) DEVICE AND METHOD FOR DETERMINATION OF AN ANALYTE IN BLOOD

(71) Applicant: HemoCue AB, Angelholm (SE)

(72) Inventors: Malin Jonsson, Lund (SE); Ekaterina Riabova, Lund (SE); Hakan Eriksson, Hjarnarp (SE); Johan Folkesson, Vejbystrand (SE)

(73) Assignee: HemoCue AB, Angelholm (SE)

( * ) Notice: Subject to any disclaimer, the term of this patent is extended or adjusted under 35 U.S.C. 154(b) by 0 days.

(21) Appl. No.: 14/317,558

(22) Filed: Jun. 27, 2014

(65) Prior Publication Data

US 2015/0377913 A1   Dec. 31, 2015

(51) Int. Cl.
| | | |
|---|---|---|
| *G01N 33/92* | (2006.01) | |
| *B01L 3/00* | (2006.01) | |
| *C12Q 1/60* | (2006.01) | |
| *G01N 21/78* | (2006.01) | |
| *G01N 21/07* | (2006.01) | |

(52) U.S. Cl.
CPC .............. *G01N 33/92* (2013.01); *B01L 3/5027* (2013.01); *B01L 3/502753* (2013.01); *C12Q 1/60* (2013.01); *G01N 21/07* (2013.01); *G01N 21/78* (2013.01); *B01L 2200/10* (2013.01); *B01L 2300/0803* (2013.01); *B01L 2300/0864* (2013.01); *B01L 2400/0406* (2013.01); *B01L 2400/0409* (2013.01); *B01L 2400/0688* (2013.01); *G01N 2201/022* (2013.01); *G01N 2333/775* (2013.01)

(58) Field of Classification Search
CPC .................................................. B01F 13/0059
See application file for complete search history.

(56) References Cited

U.S. PATENT DOCUMENTS

| | | | |
|---|---|---|---|
| 3,964,974 A | 6/1976 | Banauch et al. | |
| 4,088,448 A | 5/1978 | Lilja et al. | |
| 4,120,755 A | 10/1978 | Pierre et al. | |
| 4,181,575 A | 1/1980 | Gruber et al. | |
| 4,892,816 A | 1/1990 | Akiba et al. | |
| 5,278,047 A | 1/1994 | Lilja et al. | |
| 6,063,589 A * | 5/2000 | Kellogg et al. | 435/24 |

FOREIGN PATENT DOCUMENTS

EP   0 244 825   11/1987

* cited by examiner

*Primary Examiner* — Bin Shen
(74) *Attorney, Agent, or Firm* — Oblon, McClelland, Maier & Neustadt, L.L.P (57) ABSTRACT

A sample acquiring device, an apparatus and a method for spectrophotometric measurement of high density lipoprotein (HDL) and at least one of total cholesterol (TC), triglycerides (TG) and glucose (FPG).

17 Claims, 6 Drawing Sheets

DEVICE AND METHOD FOR DETERMINATION OF AN ANALYTE IN BLOOD

TECHNICAL FIELD

The present invention relates to a device and a method for determination of an analyte in blood. Particularly the invention concerns a sample acquiring device, an apparatus and a method for spectrophotometric measurement of high density lipoprotein and at least one of total cholesterol, triglycerides and glucose.

BACKGROUND

Triglycerides and cholesterol are the main types of fats that are transported in blood, and measurements of triglycerides and cholesterol has been proven to be an effective indicator of potential risk to atherosclerotic cardiovascular disease (CVD).

Triglyceride levels may be elevated in persons with diabetes, kidney, liver or heart diseases, and individuals with elevated triglyceride levels may be at higher risk for heart diseases.

Cholesterol is a sterol lipid essential to the cells of the body and mainly produced by the liver. As cholesterol is hydrophobic it cannot be dissolved and transported in the bloodstream directly, but is transported as part of lipoproteins, which are subdivided into three different classes based on their density. The very-low density lipoproteins (VLDL) are triglyceride-rich lipoproteins which are synthesized in the liver and ultimately converted to low-density lipoproteins (LDL), which transport most of the plasma cholesterol in humans (about 80%). The high-density lipoproteins (HDL) are lipoproteins which are involved in the catabolism of triglyceride-rich lipoproteins and the removal of cholesterol from peripheral tissues and transport to the liver. An inverse relationship between serum HDL levels and risk of CVD has been established. In particular, if the proportion of total serum cholesterol (TC) associated with HDL is low then the risk of CVD is increased.

For clinical analytical purposes in relation with atherosclerotic cardiovascular disease, the levels of the triglycerides (TG), very-low density lipoproteins (VLDL), low-density lipoproteins (LDL) and high-density lipoproteins (HDL) are of marked interest, but also the total concentration of cholesterol (TC) is important.

In connection with the introduction of several new drugs, such as statins, for hypercholesterolemia treatment during the end of 1990's, the need for point of care methods, both for screening and monitoring of cholesterol and triglycerides has increased and the clinical demands for precision and accuracy are high with a desirable imprecision of less than around 3%. It is evident that a simple, fast and temperature independent test for quantitative determination of different levels of cholesterol (total, HDL and LDL) and level of triglycerides in blood would be an important aid at doctor's offices.

Both chemical and enzymatic methods for total cholesterol measurement, HDL, LDL and triglycerides are known and measuring of total cholesterol in plasma or serum is performed in central laboratories in hospitals.

The most commonly used chemical method for total cholesterol in plasma or serum is the Liebermann-Burchard reaction, wherein cholesterol reacts as a typical alcohol with strong, concentrated acids producing a coloured substance. Today however mostly enzymatic methods are used. The enzymatic reactions start with a hydrolysis of cholesterol esters to form free cholesterol and the free cholesterol is then oxidized by the enzyme cholesterol oxidase. This enzyme is distinguished by good stability, it is easy to use and it is commercially available.

Another enzyme used in cholesterol determinations is cholesterol dehydrogenase, the use of which is disclosed in an analytical element in the patent publication EP 0 244 825. According to this publication the sample has to be incubated at a specific temperature for a prescribed time. The use of cholesterol dehydrogenase for determination of cholesterol is also disclosed in e.g. the U.S. Pat. Nos. 4,892,816 and 4,181,575. Both patents concern the determination of total cholesterol by wet chemical methods including long incubation times and defined temperatures.

For measurement of HDL, both heterogeneous methods and homogeneous methods are known. In the heterogeneous method LDL and VLDL are precipitated, and HDL aggregates are separated from the supernatant after centrifugation. In the homogeneous methods LDL and VLDL are chemically bound to block the reaction sites thereof from reacting with enzymes for cholesterol determination disclosed above.

Despite the fact that chemical measurement methods are known for total cholesterol measurement, HDL, LDL and triglycerides, there is still no quick, reliable and point of care test system designed for quantitative determination of the concentrations of TC, TG, HDL and LDL in capillary or venous whole blood. CVDs are increasing within today lifestyle and it is important to be able to receive a quick and reliable determination of these analytes.

Determination of blood glucose levels are important in relation to monitoring both diabetes type 1 and type 2 and a number of other metabolic disorders, e.g. metabolic syndrome. Metabolic syndrome is defined as a combination of several medical disorders that, when occurring together, increase the risk of developing cardiovascular disease and diabetes. The medical disorders defining metabolic syndrome are obesity, raised blood pressure, raised triglyceride value, reduced HDL cholesterol value and raised fasting plasma glucose value (FPG). Blood glucose levels in whole blood are preferably determined by the method disclosed in U.S. Pat. No. 5,278,047 wherein the whole blood is mixed with glucose dehydrogenase, diaphorase, NAD, a hemolysing agent and a redox indicator dye (e.g. MTT) and a colour change, due to the reaction between the glucose in the blood and the reagents, is measured by spectrophotometer. The determination is carried out in a disposable device (microcuvette) including a freeze-dried reagent of the type first disclosed in U.S. Pat. No. 4,088,448. The method of U.S. Pat. No. 5,278,047 is based on the method disclosed in U.S. Pat. Nos. 4,120,755 and 3,964,974 wherein glucose is determined enzymatically using glucose dehydrogenase. In U.S. Pat. No. 4,120,755 a kinetic method for glucose determination in a liquid is disclosed and in U.S. Pat. No. 3,964,974 a method for glucose determination in serum is disclosed.

In order to provide a new, fast and simple method for the determination of analytes for a proper overview of the potential risk of cardiovascular disease and/or metabolic disorders, a disposable device (microcuvette) including a dry reagent of the type first disclosed in the U.S. Pat. No. 4,088,448 was especially studied, as the use of this type of microcuvette offers several advantages.

A microcuvette permits sampling of a liquid, mixing the sample with a suitable reagent, for instance for colour development, in the same vessel as the one used for the subsequent measurement. Furthermore the sampling procedure is simplified, the number of utensils is reduced and in most cases, depending upon the type of analysis, the exactitude of the analysis is considerably improved by making the analysing procedure independent of the operating technique of the operator making the analysis. The procedure is also remarkably fast as it permits the liquid sample to be instantly mixed with the reagent and then permits measurement shortly afterwards, without time consuming intermediary steps.

SUMMARY OF INVENTION

One object of the present invention is to provide a device and a method for a fast and simple method for the determination of high-density lipoproteins (HDL) and at least one of total cholesterol (TC), triglycerides (TG) and glucose (FPG).

Another object of the present invention is to provide a device and a method for the determination of HDL and at least one of TC, TG and FPG with high accuracy and with as few utensils and as few operation techniques as possible.

The present invention concerns a sample acquiring device comprising at least one inlet for receiving a body fluid sample, at least one capillary sample reception cavity in capillary communication with said at least one inlet, a first pathway in communication with said at least one inlet and a first measurement cavity, and a second pathway in communication with said at least one inlet and a second measurement cavity, the second measurement cavity being separate from said first measurement cavity. Further, the first pathway and the second pathway are in communication with said at least one capillary sample reception cavity such that spontaneous flow from the capillary sample reception cavity is prevented and such that body fluid sample may be forced from the capillary sample reception cavity into a first centrifugation cavity of said first pathway and a first centrifugation cavity of said second pathway by subjecting the sample acquiring device to a first centrifugation. Said first centrifugation cavity of said first pathway is further in capillary communication with a first capillary cavity of said first pathway and said first centrifugation cavity of said second pathway is further in capillary communication with a first capillary cavity of said second pathway, such that at least a fraction of said body fluid sample in said first centrifugation cavity may be transferred from said first centrifugation cavities to said first capillary cavities. A precipitation agent is provided in said first capillary cavity of said second pathway. Even further said first capillary cavity of said first pathway is in communication with a second centrifugation cavity of said first pathway and said first capillary cavity of said second pathway is in communication with a second centrifugation cavity of said second pathway, such that spontaneous flow from said first capillary cavities is prevented and such that said at least a fraction of said body fluid sample from the first centrifugation cavities may be forced from the said first capillary cavity of said first pathway and into a second centrifugation cavity of said first pathway and from said first capillary cavity of said second pathway to a second centrifugation cavity of said second pathway by subjecting the sample acquiring device to a second centrifugation. Said second centrifugation cavity of said first pathway is in capillary communication with a second capillary cavity of said first pathway and said second centrifugation cavity of said second pathway is in capillary communication with a second capillary cavity of said second pathway, such that at least a fraction of said body fluid sample in said second centrifugation cavities may be transferred from said second centrifugation cavities to said second capillary cavities. Said second capillary cavity of said first pathway is further in communication with a transfer cavity of said first pathway and said second capillary cavity of said second pathway is further in communication with a transfer cavity of said second pathway, such that spontaneous flow from said second capillary cavities is prevented and such that at least a fraction of said body fluid sample in said second capillary cavities may be forced from said second capillary cavity of said first pathway into said first measurement cavity via said transfer cavity of said first pathway and from said second capillary cavity of said second pathway into said second measurement cavity via said transfer cavity of said second pathway by subjecting the sample acquiring device to a third centrifugation. At least one chromophore is provided in said second capillary cavity, in said transfer cavity or in said first measurement cavity of said first pathway, and at least one chromophore is provided in said second capillary cavity, in said transfer cavity or in said second measurement cavity of said second pathway.

In one embodiment of said sample acquiring device, said precipitation agent in said first capillary cavity of said second pathway comprises non-HDL lipoprotein complexing agents. In one embodiment said non-HDL lipoprotein complexing agents are selected from the group consisting of a) dextran sulfate and a salt of a divalent metal ion, such as $Ca^{2+}$ and $Mg^{2+}$, preferably magnesium chloride ($MgCl_2$);

b) terephthalate (PTA) and a divalent metal ion, such as $Ca^{2+}$ and $Mg^{2+}$, preferably magnesium chloride ($MgCl_2$); and c) polyethylene glycol (PEG) 6000, dextran sulfate 50,000, sodium chloride (NaCl) and a salt of a divalent metal ion, such as $Ca^{2+}$ and $Mg^{2+}$, preferably magnesium chloride ($MgCl_2$).

In one embodiment of said sample acquiring device cholesterol esterase (CE); cholesterol dehydrogenase (CDH); at least one coenzyme selected from the group consisting of β-nicotinamide adenine dinucleotide sodium salt ($NAD^+$), NADP, thio-$NAD^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more of said second capillary cavity, said transfer cavity and said second measurement cavity of said second pathway.

In one embodiment of said sample acquiring device cholesterol esterase (CE); cholesterol dehydrogenase (CDH); at least one coenzyme selected from the group consisting of β-nicotinamide adenine dinucleotide sodium salt ($NAD^+$), NADP, thio-$NAD^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in said second capillary cavity of said second pathway.

In one embodiment of said sample acquiring device said chromophore of said first pathway and said chromophore of said second pathway are redox indicator dyes. In one embodiment of said sample acquiring device MTT (3-(4,5-dimethylthiazole-2-1)-2,5-diphenyl-2H-tetrazolium bromide) is used as a redox indicator dye. MTT yields a good result when used in the inventive device, although many other tetrazolium compounds may be used. There are also several other known types of colour-changing substances, which are capable of changing colour when affected by NADH and diaphorase. Tetrazolium compounds are advantageous in that the formazan dye is formed irreversibly under normal reaction conditions.

In one embodiment of said sample acquiring device said cholesterol esterase (CE); cholesterol dehydrogenas (CDH); the coenzyme β-nicotinamide adenine dinucleotide sodium salt (NAD$^+$); and diaphorase are provided in said second capillary cavity of said second pathway.

In a further embodiment of said sample acquiring device a buffer agent is provided in said first capillary cavity of said first pathway.

In one embodiment of said sample acquiring device the buffer agent is selected from the group consisting of buffer agents providing a pH within the range of 8-11 preferably from the group consisting of tris(hydroxymethyl)aminomethane (TRIS), glycine and potassium phosphate.

In one embodiment of said sample acquiring device the buffer agent is selected from the group consisting of buffer agents providing a pH within the range of 10-11. In one embodiment of said sample acquiring device the buffer agent is glycine providing a pH within the range of 10-11.

In one embodiment of said sample acquiring device, comprising a buffer agent providing a pH within the range of 10-11 in said first capillary cavity, lipase; glycerol dehydrogenase (GYDH); at least one coenzyme selected from the group consisting of β-nicotinamide adenine dinucleotide sodium salt (NAD$^+$), NADP, thio-NAD$^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more cavities of said first pathway, wherein said one or more cavities is selected from the group consisting of said first capillary cavity, said second centrifugation cavity, said second capillary cavity, said transfer cavity, and said first measurement cavity of said first pathway, and wherein lipase and GYDH are provided in separate cavities. In one embodiment said one or more cavities is/are selected from the group consisting of said first capillary cavity and said second capillary cavity of said first pathway.

In one embodiment of said sample acquiring device the buffer agent is selected from the group consisting of buffer agents providing a pH within the range of 8-10.

In one embodiment of said sample acquiring device the buffer agent is tris(hydroxymethyl)aminomethane (TRIS) providing a pH within the range of 8-10.

In one embodiment of said sample acquiring device, comprising a buffer agent providing a pH within the range of 8-10 in said first capillary cavity, cholesterol esterase (CE); cholesterol dehydrogenase (CDH); at least one coenzyme selected from the group consisting of β-nicotinamide adenine dinucleotide sodium salt (NAD$^+$), NADP, thio-NAD$^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more cavities of said first pathway, and said one or more cavities is selected from the group consisting of said first capillary cavity, said second centrifugation cavity, said second capillary cavity, said transfer cavity, and said first measurement cavity of said first pathway. In one embodiment said one or more cavities is/are selected from the group consisting of said first capillary cavity and said second capillary cavity of said first pathway.

In one embodiment of said sample acquiring device the first centrifugation cavities of the first pathway and of the second pathway each has a lower portion and an upper portion oriented relative each other such that a centrifugation of the sample acquiring device will force any sample in the first centrifugation cavity towards the lower portion, wherein the first capillary cavity of the first pathway is in capillary communication only with the upper portion of the first centrifugation cavity of the first pathway and wherein the first capillary cavity of the second pathway is in capillary communication only with the upper portion of the first centrifugation cavity of the second pathway.

In another embodiment said sample acquiring device the second centrifugation cavity of the first pathway has a lower portion and an upper portion oriented relative each other such that a centrifugation of the sample acquiring device will force any sample in the second centrifugation cavity towards the lower portion, wherein the second capillary cavity of the first pathway is in capillary communication only with the upper portion of the second centrifugation cavity of the first pathway.

In even a further embodiment of said sample acquiring device the second centrifugation cavities of the second pathway has a lower portion and an upper portion oriented relative each other such that a centrifugation of the sample acquiring device will force any sample in the second centrifugation cavity towards the lower portion, wherein the second capillary cavity of the second pathway is in capillary communication only with the upper portion of the second centrifugation cavity of the second pathway.

In one embodiment of said sample acquiring device, said sample acquiring device has a third pathway in communication with said at least one inlet and a third measurement cavity, the third measurement cavity being separate from said first and second measurement cavity. Said third pathway is also in communication with said at least one capillary sample reception cavity such that spontaneous flow from the capillary sample reception cavity is prevented and such that body fluid sample may be forced from the capillary sample reception cavity into a first centrifugation cavity of said third pathway by subjecting the sample acquiring device to a first centrifugation. Said first centrifugation cavity of said third pathway is in capillary communication with a first capillary cavity of said third pathway, such that at least a fraction of said body fluid sample in said first centrifugation cavity may be transferred from said first centrifugation cavities to said first capillary cavities of said third pathway. Said first capillary cavity of said third pathway is in communication with a second centrifugation cavity of said third pathway, such that spontaneous flow from said first capillary cavities is prevented and such that said at least a fraction of said body fluid sample from the first centrifugation cavities may be forced from the said first capillary cavity of said third pathway and into a second centrifugation cavity of said third pathway by subjecting the sample acquiring device to a second centrifugation. Said second centrifugation cavity of said third pathway is in capillary communication with a second capillary cavity of said third pathway, such that at least a fraction of said body fluid sample in said second centrifugation cavities may be transferred from said second centrifugation cavities to said second capillary cavities. Said second capillary cavity of said third pathway is in communication with a transfer cavity of said third pathway, such that spontaneous flow from said second capillary cavities is prevented and such that at least a fraction of said body fluid sample in said second capillary cavities may be forced from said second capillary cavity of said third pathway into said first measurement cavity via said transfer cavity of said third pathway by subjecting the sample acquiring device to a third centrifugation. Also in this third pathway at least one chromophore is provided in said second capillary cavity, in said transfer cavity or in said first measurement cavity of said third pathway.

In one embodiment of the sample acquiring device having a third pathway said chromophore of said third pathway is redox indicator dyes.

In one embodiment of the sample acquiring device having a third pathway a buffer agent is provided in said first capillary cavity of said third pathway.

In one embodiment of the sample acquiring device having a third pathway the buffer agent is selected from the group consisting of buffer agents providing a pH within the range of 10-11, preferably it is glycine. Further, lipase; glycerol dehydrogenase (GYDH); at least one coenzyme selected from the group consisting of β-nicotinamide adenine dinucleotide sodium salt (NAD$^+$), NADP, thio-NAD$^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more cavities of said third pathway, wherein said one or more cavities is selected from the group consisting of said first capillary cavity, said second centrifugation cavity, said second capillary cavity, said transfer cavity, and said first measurement cavity of said third pathway, and wherein lipase and GYDH are provided in separate cavities. Preferably, said one or more cavities is selected from the group consisting of said first capillary cavity and said second capillary cavity of said third pathway.

In the same embodiment of the sample acquiring device having a third pathway with the above specified substances, said first capillary cavity of said first pathway contains a buffer agent is selected from the group consisting of buffer agents providing a pH within the range of 8-10, preferably it is tris(hydroxymethyl)aminomethane (TRIS). Further, cholesterol esterase (CE); cholesterol dehydrogenase (CDH); at least one coenzyme selected from the group consisting of β-nicotinamide adenine dinucleotide sodium salt (NAD$^+$), NADP, thio-NAD$^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more cavities of said first pathway, wherein said one or more cavities is selected from the group consisting of said first capillary cavity, said second centrifugation cavity, said second capillary cavity, said transfer cavity, and said first measurement cavity of said first pathway, Preferably, said one or more cavities is selected from the group consisting of said first capillary cavity and said second capillary cavity of said first pathway.

In one embodiment of said sample acquiring device, said sample acquiring device has a fourth pathway in communication with said at least one inlet and a fourth measurement cavity, the fourth measurement cavity being separate from said first, second and third measurement cavity. Said fourth pathway is also in communication with said at least one capillary sample reception cavity such that spontaneous flow from the capillary sample reception cavity is prevented and such that body fluid sample may be forced from the capillary sample reception cavity into a first centrifugation cavity of said fourth pathway by subjecting the sample acquiring device to a first centrifugation. Said first centrifugation cavity of said fourth pathway is in capillary communication with a first capillary cavity of said fourth pathway, such that at least a fraction of said body fluid sample in said first centrifugation cavity may be transferred from said first centrifugation cavities to said first capillary cavities of said fourth pathway. Said first capillary cavity of said fourth pathway is in communication with a second centrifugation cavity of said fourth pathway, such that spontaneous flow from said first capillary cavities is prevented and such that said at least a fraction of said body fluid sample from the first centrifugation cavities may be forced from the said first capillary cavity of said fourth pathway and into a second centrifugation cavity of said fourth pathway by subjecting the sample acquiring device to a second centrifugation. Said second centrifugation cavity of said fourth pathway is in capillary communication with a second capillary cavity of said fourth pathway, such that at least a fraction of said body fluid sample in said second centrifugation cavities may be transferred from said second centrifugation cavities to said second capillary cavities. Said second capillary cavity of said fourth pathway is in communication with a transfer cavity of said fourth pathway, such that spontaneous flow from said second capillary cavities is prevented and such that at least a fraction of said body fluid sample in said second capillary cavities may be forced from said second capillary cavity of said fourth pathway into said first measurement cavity via said transfer cavity of said fourth pathway by subjecting the sample acquiring device to a third centrifugation. Also in this fourth pathway at least one chromophore is provided in said second capillary cavity, in said transfer cavity or in said first measurement cavity of said fourth pathway.

In one embodiment of the sample acquiring device having a fourth pathway said chromophore of said fourth pathway is redox indicator dyes.

In one embodiment of the sample acquiring device having a fourth pathway glucose dehydrogenase (GDH); mutarotase; at least one coenzyme selected from the group consisting of β-nicotinamide adenine dinucleotide sodium salt (NAD$^+$), NADP, thio-NAD$^+$, thio-NADP, nicotinamide-purine dinucleotide, nicotinamide-methylpurine dinucleotide and nicotinamide-2-chloro-methylpurine dinucleotide; and at least one enzyme selected from the group consisting of diaphorase, phenazine methosulfate, phenazine ethosulfate, phenazine phenosulfate and Meldola blue; are provided in one or more cavities of said fourth pathway, wherein said one or more cavities is selected from the group consisting of said first capillary cavity, said second centrifugation cavity, said second capillary cavity, said transfer cavity, and said first measurement cavity of said fourth pathway. Preferably, said one or more cavities is selected from the group consisting of said first capillary cavity and said second capillary cavity of said fourth pathway.

The present invention further concerns an apparatus for spectrophotometric measurements of high density lipoprotein (HDL) and at least one of total cholesterol (TC), triglycerides (TG) and glucose (FPG). According to the invention the apparatus has a rotatable disc adapted to be rotated by an electrical motor according to a predetermined cycle, wherein the rotatable disc has a cuvette receiving cavity adapted for receiving a sample acquiring device previously described, said cuvette receiving cavity being located off centre on said rotatable disc, and wherein said apparatus has optical measurement units adapted for spectrophotometric measurements of at least said first and second measurement cavity of said sample acquiring device.

In one embodiment of the present invention said apparatus has optical measurement units adapted for spectrophotometric measurement of an additional third measurement cavity of said sample acquiring device.

In one embodiment of the present invention said apparatus has optical measurement units adapted for spectrophotometric measurement of an additional fourth measurement cavity of said sample acquiring device.

The present invention further concerns a method for spectrophotometric measurements of high density lipoprotein (HDL) and at least one of total cholesterol (TC), triglycerides (TG) and glucose (FPG). According to the invention the method comprises inserting a sample acquiring device according to any of the above identified embodiments thereof into a cuvette receiving cavity on a rotatable disc in an apparatus according to any of the above identified embodiments; rotating said rotatable disc at 4000-5000 rpm for 30-120 seconds, forcing the body fluid sample in a sample reception cavity into a first centrifugation cavity of each pathway respectively; stopping or decreasing the rotation to remove or decrease the centrifugal force acting on the body fluid sample in the sample acquiring device for 15-90 seconds enabling capillary action to transfer at least a fraction of the body fluid sample from the first centrifugation cavity to a first capillary cavity of each pathway respectively; rotating said rotatable disc at 4000-5000 rpm for 30-90 seconds, forcing the body fluid sample in the first capillary cavity into a second centrifugation cavity of each pathway respectively; stopping or decreasing the rotation to remove or decrease the centrifugal force acting on the body fluid sample in the sample acquiring device for 15-90 seconds enabling capillary action to transfer at least a fraction of the body fluid sample from the second centrifugation cavity to a second capillary cavity of each pathway respectively; rotating said rotatable disc at 2500-4000 rpm for 5-30 seconds, forcing the body fluid sample in the second capillary cavity into a transfer cavity and further into a measurement cavity of each pathway respectively; and thereafter decreasing the rotation of said rotatable disc to 10-20 rpm allowing the sample acquiring device to rotate past the optical measurement units over and over again until steady measurement results have been recorded for all measurement cavities.

DESCRIPTION OF THE DRAWINGS

The invention will by way of example be described in more detail with reference to the appended schematic drawings, which shows a presently preferred embodiment of the invention.

DETAILED DESCRIPTION OF PREFERRED EMBODIMENTS

Figure 1:
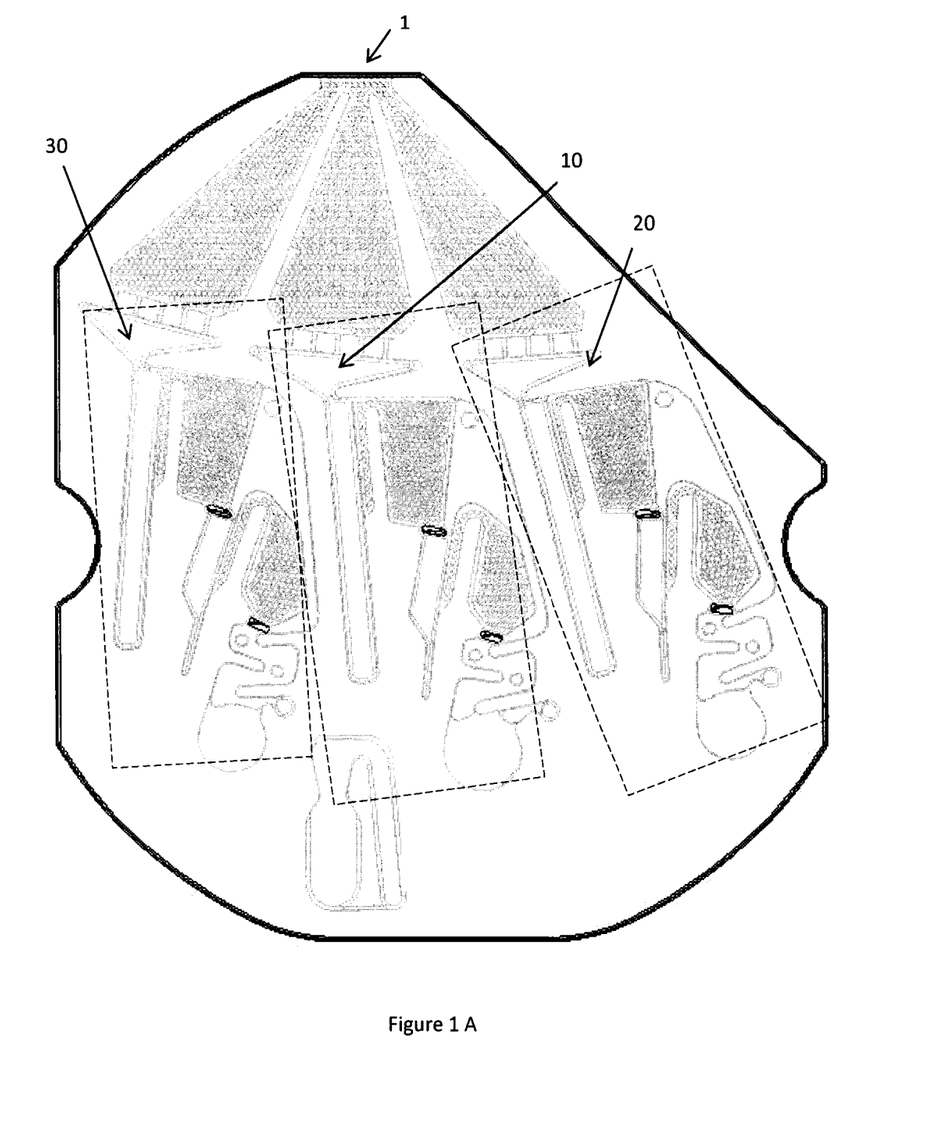
FIGS. 1A and 1B shows in a plane projection a sample acquiring device, a so-called microcuvette, provided with three analysis pathways.

In FIGS. 1A and 1B, a sample acquiring device according to one embodiment of the present invention is shown in a plane projection. The sample acquiring device has three parallel analysis pathways, marked with dotted squares as 10, 20, and 30, FIG. 1A. The sample acquiring device has an inlet 1, and this inlet is adapted for receiving the body fluid sample, which may be whole blood, diluted blood or plasma. The inlet 1 is in capillary communication with three different capillary sample reception cavities 12, 22, and 32, one capillary sample reception cavity for each pathway, FIG. 1B. Thus, as the body fluid sample enters through the inlet 1, the fluid is drawn into the three different capillary sample reception cavities 12, 22, 32 by a capillary force.

As mentioned above, this embodiment has three different pathways, each pathway being in communication with the inlet 1 and one measurement cavity each. Thus, the first pathway 10 is in communication with the inlet 1 and a first measurement cavity 11, the second pathway 20 is in communication with the inlet 1 and a second measurement cavity 21, and the third pathway 30 is in communication with the inlet 1 and a third measurement cavity 31. All measurement cavities 11, 21, and 31 are separated from each other.

Figure 2:
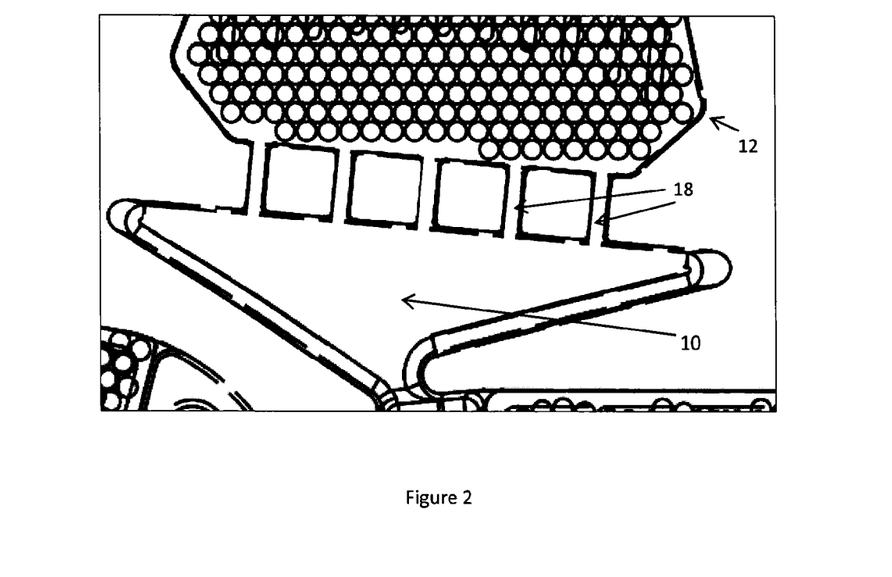
FIG. 2 shows an enlargement of a portion of one of the capillary sample reception cavities and the associated capillary lock of the sample acquiring device shown in FIGS. 1A and 1B.

Respective pathway 10, 20, and 30 is in communication with respective capillary sample reception cavity 12, 22, and 32 in a way which prevents spontaneous flow from the capillary sample reception cavity into the pathway. As shown in FIG. 2, the sample acquiring device is provided with several narrow channels 18 between the sample reception cavity 12 and the pathway 10. As shown in FIGS. 1A and 1B, similar narrow channels are provided between the sample reception cavity and pathway of the other pathways 20 and 30. Each such narrow channel provides the function as a capillary lock and will in the following be referred to as a capillary lock.

Each capillary lock is in fluid communication with respective sample reception cavity 12, 22 and 32 of respective pathway 10, 20 and 30. Each capillary lock increases the pressure needed to transport the body fluid sample through the capillary lock such that the capillary forces present upstream and in the capillary lock are not sufficient to provide a capillary flow of the body fluid sample from the sample reception cavity to respective pathway. Thus, in order to provide a flow from the sample reception cavity or cavities 12, 22 and 32 into respective pathway 10, 20 and 30, the sample acquiring device must be subjected to a centrifugation. In the shown embodiment there is a separate sample reception cavity for respective pathway and there is one capillary lock for each pathway. That is, in the shown design there are three separate sample reception cavities, each being associated with a separate capillary lock and a separate pathway. In an alternative design there is provided a single sample reception cavity with a capillary lock for respective pathway. That is, in the shown design it would be one sample reception cavity provided with three capillary locks, each in communication with a separate pathway.

The capillary action in the sample reception cavity 12, 22 and 32 is provided by forming the sample reception cavity from two essentially parallel surfaces being arranged close to each other. The distance between the surfaces is chosen to provide a capillary action. In the shown design the distance between the surfaces is 0.25 mm. It is preferred that the distance between them is between 0.10 and 0.50 mm.

The capillary lock has a rectangular cross-section with a height of 0.25 mm and a width of 0.20 mm. It is preferred that the width of the capillary lock is between 0.010 and 5 mm.

It is contemplated that the capillary lock may be formed using other cross-sectional shapes, such as ellipsoid, circular, or quadratic. The capillary lock has a maximum width being decided by the width of the sample reception cavity 12, 22 and 32 and the width of the respective pathway 10, 20 and 30.

In a first embodiment there is provided a single capillary lock between the respective sample reception cavity and respective pathway. The single lock may be placed on the left side, on the right side or in the middle of the opening between the sample reception cavity 12, 22 and 32 and respective pathway 10, 20 and 30. In a second embodiment there is provided a plurality of capillary locks between the respective sample reception cavity and respective pathway. In the disclosed embodiment there are five capillary locks between respective sample reception cavity and respective pathway. It is preferred that the total cross-sectional area of the capillary locks is of the same order, most preferably the same, between one sample reception cavity and respective pathway compared to the same or another sample reception cavity and another respective pathway.

In each pathway respective capillary reception cavity 12, 22, and 32 is in communication with a first centrifugation cavity 13, 23 and 33, having a capillary lock as disclosed above. Thus, the body fluid sample may only enter into the first centrifugation cavity 13, 23 and 33 by subjecting the sample acquiring device to a first centrifugation. Thus, the body fluid sample in the capillary reception cavity 12 in the first pathway 10 enters the first centrifugation cavity 13 when being subjected to a first centrifugation, the body fluid sample in the capillary reception cavity 22 in the second pathway 20 enters the first centrifugation cavity 23 when being subjected to a first centrifugation, and the body fluid sample in the capillary reception cavity 32 in the third pathway 30 enters the first centrifugation cavity 33 when being subjected to a first centrifugation.

After a sufficient time of centrifugation the rotation is stopped or decreased to remove or decrease the centrifugal force acting on the body fluid sample in the sample acquiring device within the first centrifugation cavity 13, 23, 33.

The first centrifugation cavity 13, 23, 33 of respective pathway 10, 20 and 30 is in capillary communication with a respective first capillary cavity 14, 24, and 34, such that at least a fraction of the body fluid sample present in the first centrifugation cavity 13, 23, and 33 may be transferred from said first centrifugation cavity to said first capillary cavity. In the embodiment shown in FIG. 1B, the first centrifugation cavities 13, 23, 33 each have a lower portion and an upper portion oriented relative each other such that a centrifugation of the sample acquiring device will force any sample in the first centrifugation cavities towards the lower portions thereof. When the body fluid sample is whole blood, the blood cells will gather in the lower part of the first centrifugation cavities during the centrifugation, while the blood plasma will be positioned in the upper part of the first centrifugation cavities 13, 23, 33. The first capillary cavity 14, 24, 34 of each pathway is only in capillary communication with the upper portion of the first centrifugation cavity of each pathway. Thus, it is only the plasma fraction of the whole blood sample which will be transferred into the first capillary cavity of each pathway.

In the first capillary cavity 24 of the second pathway 20 a precipitation agent is provided, and in a preferred embodiment this precipitation agent is non-HDL lipoprotein complexing agents, preferably selected from the group consisting of dextran sulfate and a salt of a divalent metal ion, such as $Ca^{2+}$ and $Mg^{2+}$, preferably magnesium chloride ($MgCl_2$); terephthalate (PTA) and a divalent metal ion, such as $Ca^{2+}$ and $Mg^{2+}$, preferably magnesium chloride ($MgCl_2$); and polyethylene glycol (PEG) 6000, dextran sulfate 50,000, sodium chloride (NaCl) and a salt of a divalent metal ion, such as $Ca^{2+}$ and $Mg^{2+}$, preferably magnesium chloride ($MgCl_2$). In one embodiment the precipitation agent is dextran sulfate 50,000 and $MgCl_2$. With this precipitation agent, HDL lipoprotein will remain in free form within the plasma sample while LDL and VLDL lipoprotein will become complex bound and precipitate within the plasma fraction present in the first capillary cavity 24 of the second pathway 20.

In the first capillary cavity 14 of the first pathway 10 a buffer agent selected from the group consisting of buffer agents providing a pH within the range of 8-10, and preferably the buffer agent is tris(hydroxymethyl)-aminomethane (TRIS).

In the first capillary cavity 34 of the third pathway 30 a buffer agent selected from the group consisting of a buffer agent providing a pH within the range of 10-11 is provided. Preferably the buffer agent is glycine. Further, in the first capillary cavity 34 also one enzyme chosen from the group consisting of lipase and glycerol dehydrogenase (GYDH) is provided, preferably GYDH is provided in the first capillary cavity.

In each pathway respective first capillary cavity 14, 24, and 34 is in communication with a respective second centrifugation cavity 15, 25 and 35. A capillary lock is provided between respective first capillary cavity 14, 24, and 34 and respective second centrifugation cavity 15, 25 and 35. Thus, the plasma fraction sample may only enter into the second centrifugation cavity 15, 25 and 35 by subjecting the sample acquiring device to a second centrifugation. Thus, the plasma fraction sample with a buffer in the first capillary cavity 14 in the first pathway 10 enters the second centrifugation cavity 15 when being subjected to a second centrifugation, the plasma fraction sample with precipitated LDL and VLDL lipoproteins and free HDL in the first capillary cavity 24 in the second pathway 20 enters the second centrifugation cavity 25 when being subjected to a second centrifugation, and the plasma fraction sample with buffer and an enzyme, preferably GYDH in the first capillary cavity 34 in the third pathway 30 enters the second centrifugation cavity 35 when being subjected to a second centrifugation.

In this embodiment the capillary lock between the first capillary cavity and the second centrifugation cavity is provided by having an increased distance between the surfaces forming the pathway in a borderline between the first capillary cavity and the second centrifugation cavity.

After a sufficient time of centrifugation the rotation is again stopped or decreased to remove or decrease the centrifugal force acting on the plasma fraction samples in the sample acquiring device within each second centrifugation cavity 15, 25, 35.

Respective second centrifugation cavity 15, 25, 35 of each pathway 10, 20 and 30 is in capillary communication with a respective second capillary cavity 16, 26, and 36, such that at least a fraction of the plasma fraction sample present in the second centrifugation cavity 15, 25, and 35 may be transferred from said second centrifugation cavity to said second capillary cavity 16, 26, and 36. In the shown embodiment in FIG. 1B, the second centrifugation cavities 15, 25, 35 also have a lower portion and an upper portion oriented relative each other such that a centrifugation of the sample acquiring device will force any sample in the second centrifugation cavities towards the lower portion thereof. In the second pathway, the precipitated LDL and VLDL lipoproteins will gather in the lower part of the second centrifugation cavity 25 of the second pathway 20 during the centrifugation, while the plasma fraction containing free HDL will be positioned in the upper part of the second centrifugation cavity 25. The respective second capillary cavity 16, 26, 36 of each pathway 10, 20, 30 is only in capillary communication with the upper portion of the respective second centrifugation cavity of each pathway. Thus, it is only a small fraction of the plasma fraction sample which will be transferred into the second capillary cavity of each pathway, and especially in the second pathway, the precipitated LDL and VLDL lipoproteins will not be transferred into the second capillary cavity 26 of the second pathway 20.

In the second capillary cavity 26 of the second pathway 20 cholesterol esterase (CE); cholesterol dehydrogenase (CDH), a coenzyme β-nicotinamide adenine dinucleotide sodium salt (NAD$^+$) and diaphorase is provided together with a chromophore, preferably a redox indicator dye, such as 3-(4,5-dimethylthiazole-2-1)-2,5-diphenyl-2H-tetrazolium bromide (MTT).

The reactions taking place within the second capillary cavity 26 of the second pathway 20 are the following (enzymes for the different reactions are given within parentheses after each reaction):

The amount of formed formazan is in direct correlation with the amount of HDL in the body fluid sample.

In the second capillary cavity 16 of the first pathway 10 also cholesterol esterase (CE); cholesterol dehydrogenase (CDH), a coenzyme β-nicotinamide adenine dinucleotide sodium salt (NAD$^+$) and diaphorase is provided together with a chromophore, preferably a redox indicator dye, such as 3-(4,5-dimethylthiazole-2-1)-2,5-diphenyl-2H-tetrazolium bromide (MTT).

The reactions taking place within the second capillary cavity 16 of the first pathway 10 are the following (enzymes for the different reactions are given within parentheses after each reaction):

Thus, the reactions are similar to the reactions in the second pathway with the exception that the amount of formed formazan is in direct correlation with the amount of total cholesterol (TC) in the body fluid sample.

In the second capillary cavity 36 of the third pathway 30 one of lipase and glycerol dehydrogenase (GYDH) is provided, preferably lipase, together with coenzyme β-nicotinamide adenine dinucleotide sodium salt (NAD$^+$), diaphorase and a chromophore, preferably a redox indicator dye, such as 3-(4,5-dimethylthiazole-2-1)-2,5-diphenyl-2H-tetrazolium bromide (MTT).

The reactions taking place with the optional start within the first capillary cavity 34 (when containing lipase), but preferably starting within the second capillary cavity 36 of the third pathway 30 are the following (enzymes for the different reactions are given within parentheses after each reaction).

The formed formazan is in direct correlation with the amount of triglyceride in the body fluid sample.

Respective second capillary cavity 16, 26, 36 is in communication with a respective transfer cavity 17, 27 and 37 such that spontaneous flow from the capillary cavity 16, 26 and 36 is prevented. Also here a capillary lock is provided in the borderline between the second capillary cavity 16, 26, 36 and the transfer cavity 17, 27, 37. Thus, the plasma fractions containing the reagents may only enter into the transfer cavity 17, 27 and 37 by subjecting the sample acquiring device to a third centrifugation. Thus, the plasma fraction containing the reagents in the second capillary cavity 16 in the first pathway 10 enters the transfer cavity 17 when being subjected to a third centrifugation, the plasma fraction containing the reagents in the second capillary cavity 26 in the second pathway 20 enters the transfer cavity 27 when being subjected to a third centrifugation, and the plasma fraction containing the reagents in the second capillary cavity 36 in the third pathway 30 enters the transfer cavity 37 when being subjected to a third centrifugation.

In this embodiment the capillary lock between the second capillary cavity and the transfer cavity is provided by having an increased distance between the surfaces forming the pathway in a borderline between the second capillary cavity and the transfer cavity.

From respective transfer cavity 17, 27 and 37, the plasma fraction containing the reagents further enters the first measurement cavity 11, second measurement cavity 21 and third measurement cavity 31, respectively. Thus, the plasma fraction in transfer cavity 17 enters the first measurement cavity 11, the plasma fraction in the transfer cavity 27 enters the second measurement cavity 21, and the plasma fraction in the transfer cavity 37 enters the third measurement cavity 31.

After a sufficient time of centrifugation the rotation is decreased to decrease the centrifugal force acting on the plasma fraction samples in the measurement cavities 11, 21, and 31, and spectrophotometric measurements are performed on the plasma fractions within the measurement cavities 11, 21 and 31.

In one embodiment of the sample acquiring device some cavity surfaces are covered with a surfactant/wetting agent to lower the surface tension of the cavity surfaces. With such a surfactant/wetting agent the capillary forces are enhanced in comparison with a surface not covered with surfactant/wetting agent. In one embodiment of the sample acquiring device, at least one wall of each capillary cavity is covered with a surfactant/wetting agent. A surfactant/wetting agent also has influence on the distribution of reagents when being applied to the surfaces during manufacturing of the sample acquiring device, such reagents being buffers, enzymes, coenzymes and chromophores.

In one embodiment of the sample acquiring device, the distance between the surfaces forming the second measurement cavity is larger than the distance between the surfaces forming the first measurement cavity.

In one embodiment of the sample acquiring device, the distance between the surfaces forming the second measurement cavity is the same as the distance between the surfaces forming the first measurement cavity.

In the embodiment of the sample acquiring device having a third pathway with a third measurement cavity, the distance between the surfaces forming the first measurement cavity is smaller than the distance between the surfaces forming the second and third measurement cavity, respectively.

Figure 4:
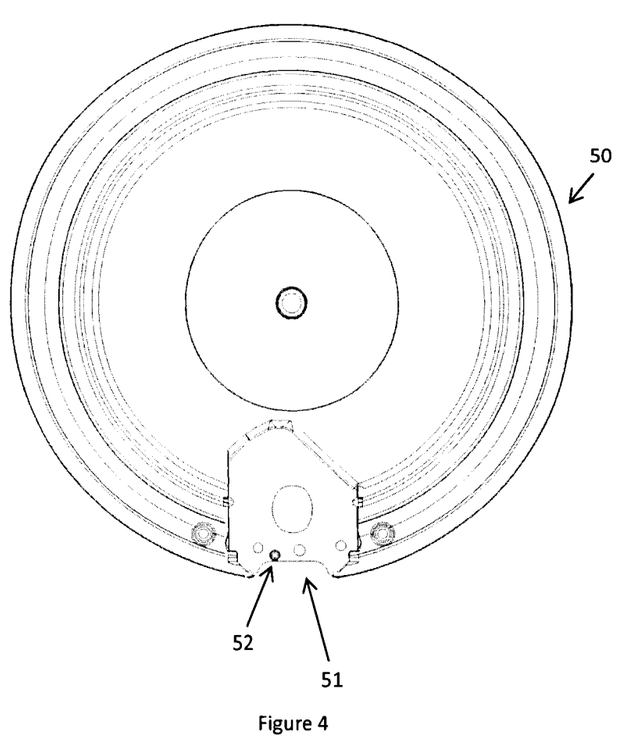
FIG. 4 shows the rotatable disc of the analysis apparatus.

The sample acquiring device is adapted to be placed in a cuvette receiving cavity 51 located off centre on a rotatable disc 50 in the apparatus according to the invention. The rotatable disc 50 is adapted to be rotated by an electrical motor according to a predetermined cycle.

In one embodiment of the method for spectrophotometric measurements the sample acquiring device is inserted into the cuvette receiving cavity 51 of the rotatable disc 50.

Then the rotatable disc 50 is rotated at 4000-5000 rpm for 30-120 seconds, thereby forcing the body fluid sample in the sample reception cavity through the capillary locks into the first centrifugation cavity of respective pathway.

Then the rotation is stopped or decreased such that no or a decreased centrifugal force acts on the body fluid sample in the sample acquiring device. This non-centrifugal state is provided in 15-90 seconds, allowing capillary action to transfer at least a fraction of the body fluid sample from the first centrifugation cavity to a first capillary cavity of respective pathway.

Thereafter the disc 50 is rotated at 4000-5000 rpm for 30-90 seconds, thereby forcing at least a fraction of the body fluid sample in the first capillary cavity into the second centrifugation cavity of respective pathway.

Then the rotation is stopped or decreased such that no or a decreased centrifugal force acts on the body fluid sample in the sample acquiring device. This non-centrifugal state is provided in 15-90 seconds, allowing capillary action to transfer at least a fraction of the body fluid sample from the second centrifugation cavity to a second capillary cavity of respective pathway.

Thereafter the disc 50 is rotated at 2500-4000 rpm for 5-30 seconds, thereby forcing a at least a fraction of the body fluid sample in the second capillary cavity into a transfer cavity and further into a measurement cavity of respective pathway.

Thereafter the rotation is decreased to 10-20 rpm allowing the microcuvette to rotate past an analysis point over and over again. This rotation is performed until the final reactions have had time to be completed and until the sufficient number of readings has been achieved for all measurement cavities.

Figure 3:
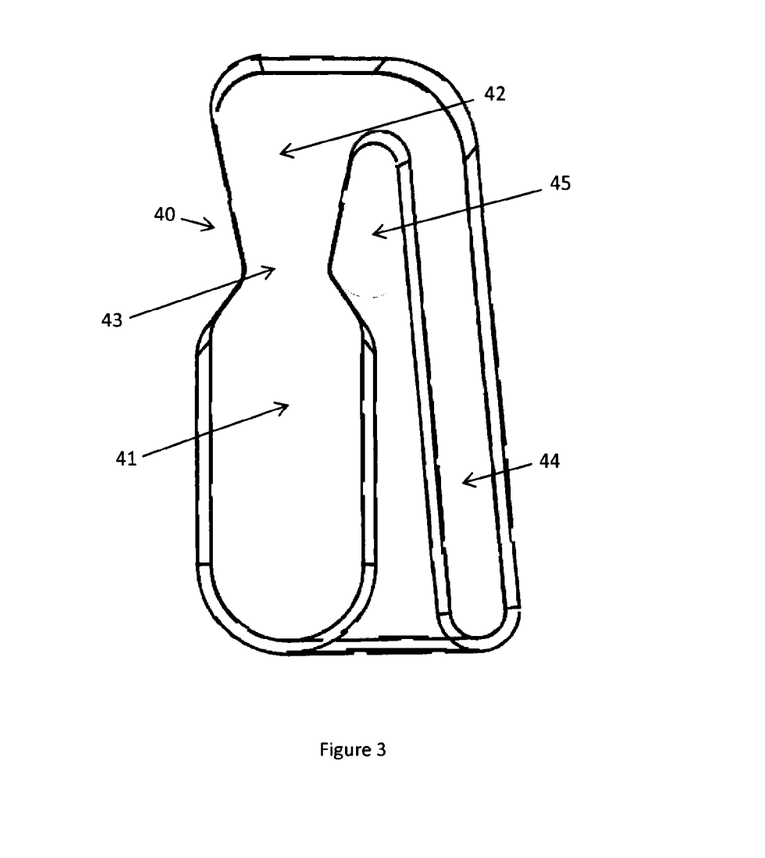
FIG. 3 shows an enlargement of the locking portion at the bottom of the sample acquiring device shown in FIGS. 1A and 1B.

The apparatus for spectrophotometric measurements according to the invention has centrifugation platform and an optic unit. Said centrifugation platform has a rotatable disc 50, as shown in FIG. 4. The rotatable disc is adapted to be rotated by an electrical motor according to a predetermined cycle. The rotatable disc 50 has a cuvette receiving cavity 51 adapted for receiving a sample acquiring device according to the invention, and said cuvette receiving cavity is located off centre on said rotatable disc 50. In order to securely holding the sample acquiring device in place in the cuvette receiving cavity 51 of the rotatable disc 50, the sample acquiring device is further provided with a track 40, as shown in FIGS. 1A and 1B and FIG. 3. Said track is adapted to interact with a protruding member 52 fastened or integrally shaped with the rotatable disc 50 shown in FIG. 4. The protruding member 52 is provided inside the cuvette receiving cavity 51. In the preferred embodiment the protruding member 52 is a pin shaped member. The track 40 is shaped with an entrance section 41 and a locking section 42. The entrance section 41 has a width being larger than the width of the locking section 42. The entrance section 41 has a width large enough to allow easy entrance of the protruding member 52 into the track 40. The locking section 42 has a width small enough to securely interact with the protruding member 52 helping to keep the sample acquiring device in place in the cuvette receiving cavity 51. The entrance section 41 is located outside the locking section 42 as viewed in the coordinate system of the rotatable disc 50. A direction extending from the entrance section 41 towards the locking section 42 will be pointing essentially in the opposite direction compared to the direction the centrifugal cavities of the sample acquiring device are adapted to receive the body fluid sample as the sample acquiring device is subjected to centrifugation. As the sample acquiring device is placed in the cuvette receiving cavity 51, the protruding member 52 enters into the entrance section 41. Thereafter the user pushes the sample acquiring device outwardly, but still within the cuvette receiving cavity 51. If the user neglects to push the sample acquiring device outwardly as previously described, the sample acquiring device will be pushed outwardly when the centrifugation is started by the centrifugal force acting on the sample acquiring device. The relative movement of the, relative to the cuvette receiving cavity 51, still-standing protruding member 52 will make the protruding member 52 entering into the locking section 42 of the track 40. In order to provide a secure and distinct locking mechanism, the track 40 may be provided with a waist section 43 between the entrance section 41 and the locking section 42, the waist section 43 having a width smaller than the width of the locking section 42. The track 40 is further provided with a second section 44, being connected to the locking section 42 and extending along and at a distance from the locking section 42, the waist section 43 (if any) and at least a part of the entrance section 41. Thereby will one of the walls of the track 40, at the transition (i.e. waist section 43 if provided) between the entrance section 41 and the locking section 42, be formed of a wall portion 45 having a free end facing the connection between the second section 44 and the locking section 42. The wall 45 will be shaped as a finger. The finger 45 will be pointing inwardly relative to the rotatable disc 50. The finger 45 will be pointing essentially in the opposite direction compared to the flow direction in the centrifugal cavities of the sample acquiring device which are adapted to receive the body fluid sample as the sample acquiring device is subjected to centrifugation. The finger 45 will provide resilience to the wall allowing the protruding member 52 to temporarily displace the wall 45 as the protruding member 52 moves from the entrance section 41 to the locking section 42. In one embodiment the track 40 is provided in one of the surfaces of the sample acquiring device, i.e. with a track depth smaller than the thickness of the sample acquiring device. In a preferred embodiment the track 40 is provided through-out the thickness of a plate shaped member forming one of the major surfaces of the sample acquiring device. In this preferred embodiment the track 40 is not formed in the plate shaped member forming the other major surface of the sample acquiring device. Preferably the two plate shaped members are not attached to each other where the wall 45 with the free end (the finger) is formed, thereby providing the resilience of the wall 45 (finger). In a preferred embodiment the track is provided in the major surface being adapted to be positioned facing the rotatable disc 50. In another embodiment the track 40 is provided through-out the thickness of the sample acquiring device.

Said optical unit of said apparatus is adapted for spectrophotometric measurements of at least said first and second measurement cavity of said sample acquiring device, and if present, also of said third and fourth measurement cavities. The measured values from said first and second and optional third and fourth measurement cavities are thereafter software processed and displayed on a communication platform of said apparatus. In different embodiments of said apparatus according to the present invention HDL measurements are communicated together with TC measurements and/or TG measurements and/or FPG measurements. LDL values may also be displayed, in this case being a calculated value using the HDL and TC measurements.

Figure 5:
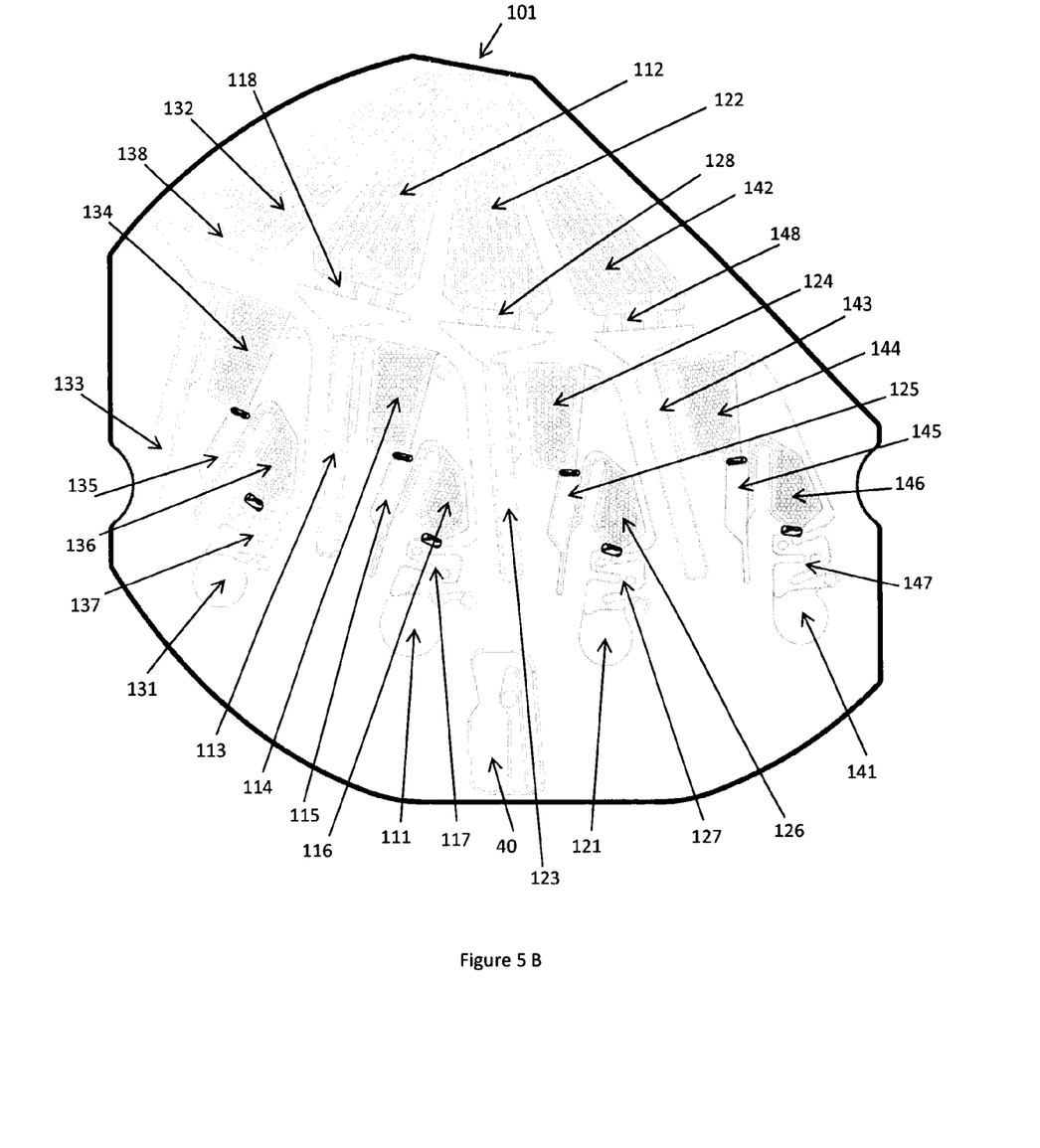
FIGS. 5A and 5B shows in a plane projection a sample acquiring device, a so-called microcuvette, provided with four analysis pathways.
Figure 5A:
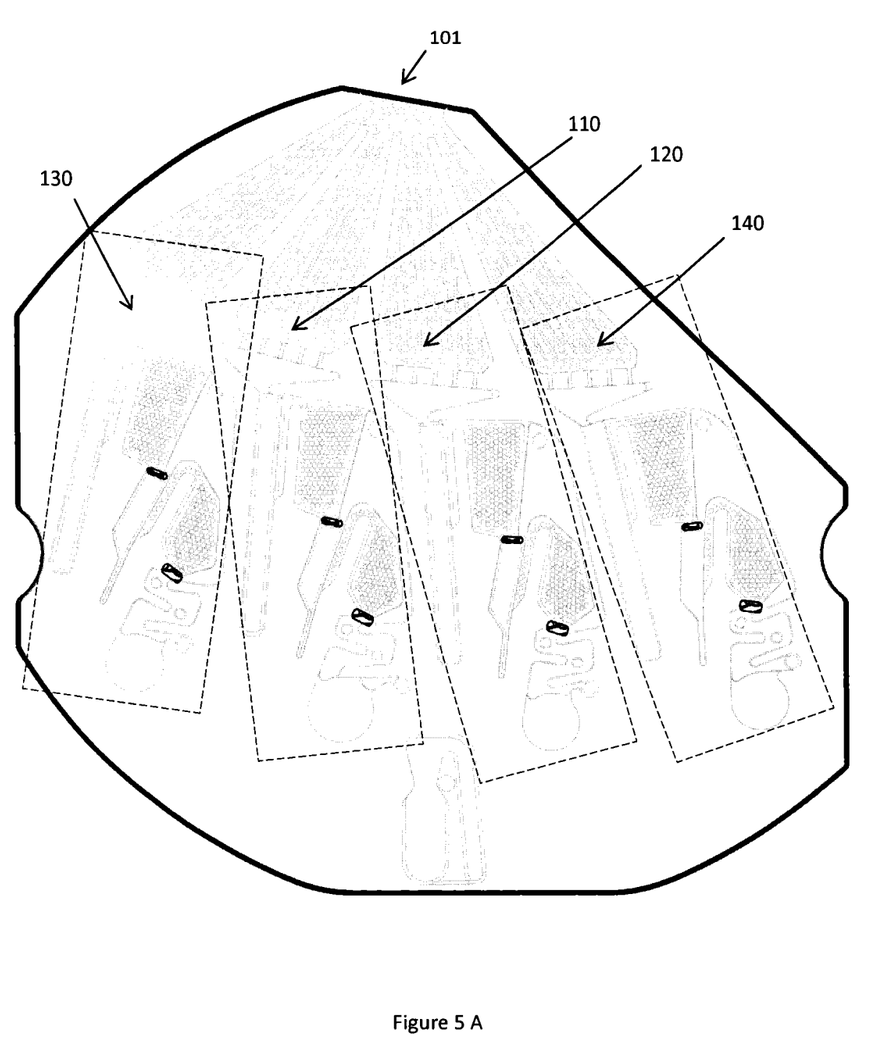

In FIGS. 5A and 5B, a sample acquiring device according to another embodiment of the present invention is shown in a plane projection. The sample acquiring device has four parallel analysis pathways, marked with dotted squares as 110, 120, 130, and 140, FIG. 5A. The sample acquiring device has an inlet 101, and this inlet is adapted for receiving the body fluid sample, which may be whole blood, diluted blood or plasma. The inlet 101 is in capillary communication with four different capillary sample reception cavities 112, 122, 132, and 142, one capillary sample reception cavity for each pathway, FIG. 5B. Thus, as the body fluid sample enters through the inlet 101, the fluid is drawn into the four different capillary sample reception cavities 112, 122, 132, 142 by a capillary force. Thus, the first pathway 110 is in communication with the inlet 101 and a first measurement cavity 111, the second pathway 120 is in communication with the inlet 101 and a second measurement cavity 121, the third pathway 130 is in communication with the inlet 101 and a third measurement cavity 131 and the fourth pathway 140 is in communication with the inlet 101 and a fourth measurement cavity 141. All measurement cavities 111, 121, 131, and 141 are separated from each other.

Respective pathway 110, 120, 130, and 140 is in communication with respective capillary sample reception cavity 112, 122, 132, and 142 in a way which prevents spontaneous flow from the capillary sample reception cavity into the pathway. The sample acquiring device is provided with several narrow channels 118, 128, 138, and 148 between respective sample reception cavity 112, 122, 132, and 142 and respective pathway 110, 120, 130, and 140. Each such narrow channel provides the function as a capillary lock and will in the following be referred to as a capillary lock.

Each capillary lock is in fluid communication with respective sample reception cavity 112, 122, 132, and 142 and respective pathway 110, 120, 130, and 140. Each capillary lock increases the pressure needed to transport the body fluid sample through the capillary lock such that the capillary forces present upstream and in the capillary lock are not sufficient to provide a capillary flow of the body fluid sample from the sample reception cavity to respective pathway. Thus, in order to provide a flow from the sample reception cavity or cavities 112, 122, 132, and 142 into respective pathway 110, 120, 130, and 140, the sample acquiring device must be subjected to a centrifugation. In the shown embodiment there is a separate sample reception cavity for respective pathway and there is one capillary lock for each pathway. That is, in the shown design there are four separate sample reception cavities, each being associated with a separate capillary lock and a separate pathway. In an alternative design there is provided a single sample reception cavity with a capillary lock for respective pathway. That is, in the shown design it would be one sample reception cavity provided with four capillary locks, each in communication with a separate pathway.

The capillary action in the sample reception cavity 112, 122, 132 and 142 is provided by forming the sample reception cavity from two essentially parallel surfaces being arranged close to each other. The distance between the surfaces is chosen to provide a capillary action. In the shown design the distance between the surfaces is 0.25 mm. It is preferred that the distance between them is between 0.10 and 0.50 mm.

The capillary lock has a rectangular cross-section with a height of 0.25 mm and a width of 0.20 mm. It is preferred that the width of the capillary lock is between 0.010 and 5 mm.

It is contemplated that the capillary lock may be formed using other cross-sectional shapes, such as ellipsoid, circular, or quadratic. The capillary lock has a maximum width being decided by the width of the sample reception cavity 112, 122, 132 and 142 and the width of the respective pathway 110, 120, 130, and 140.

In a first embodiment there is provided a single capillary lock between the respective sample reception cavity and respective pathway. The single lock may be placed on the left side, on the right side or in the middle of the opening between the sample reception cavity 112, 122, 132 and 142 and respective pathway 110, 120, 130, and 140. In a second embodiment there is provided a plurality of capillary locks between the respective sample reception cavity and respective pathway. In the disclosed embodiment there are five capillary locks between respective sample reception cavity and respective pathway. It is preferred that the total cross-sectional area of the capillary locks is of the same order, most preferably the same, between one sample reception cavity and respective pathway compared to the same or another sample reception cavity and another respective pathway.

In each pathway respective capillary reception cavity 112, 122, 132 and 142 is in communication with a first centrifugation cavity 113, 123, 133 and 143 having a capillary lock as disclosed above. Thus, the body fluid sample may only enter into the first centrifugation cavity 113, 123, 133 and 143 by subjecting the sample acquiring device to a first centrifugation. Thus, the body fluid sample in the capillary reception cavity 112 in the first pathway 110 enters the first centrifugation cavity 113 when being subjected to a first centrifugation, the body fluid sample in the capillary reception cavity 122 in the second pathway 120 enters the first centrifugation cavity 123 when being subjected to a first centrifugation, the body fluid sample in the capillary reception cavity 132 in the third pathway 130 enters the first centrifugation cavity 133 when being subjected to a first centrifugation, and the body fluid sample in the capillary reception cavity 142 in the fourth pathway 140 enters the first centrifugation cavity 143 when being subjected to a first centrifugation.

After a sufficient time of centrifugation the rotation is stopped or decreased to remove or decrease the centrifugal force acting on the body fluid sample in the sample acquiring device within the first centrifugation cavity 113, 123, 133, 143.

The first centrifugation cavity 113, 123, 133, 143 of respective pathway 110, 120, 130, and 140 is in capillary communication with a respective first capillary cavity 114, 124, 134, and 144, such that at least a fraction of the body fluid sample present in the first centrifugation cavity 113, 123, 133 and 143 may be transferred from said first centrifugation cavity to said first capillary cavity. In the embodiment shown in FIG. 5B, the first centrifugation cavities 113, 123, 133, 143 each have a lower portion and an upper portion oriented relative each other such that a centrifugation of the sample acquiring device will force any sample in the first centrifugation cavities towards the lower portions thereof. When the body fluid sample is whole blood, the blood cells will gather in the lower part of the first centrifugation cavities during the centrifugation, while the blood plasma will be positioned in the upper part of the first centrifugation cavities 113, 123, 133, 143. The first capillary cavity 114, 124, 134, 144 of each pathway is only in capillary communication with the upper portion of the first centrifugation cavity of each pathway. Thus, it is only the plasma fraction of the whole blood sample which will be transferred into the first capillary cavity of each pathway.

In the first capillary cavity 124 of the second pathway 120 a precipitation agent is provided, and in a preferred embodiment this precipitation agent is non-HDL lipoprotein complexing agents, preferably selected from the group consisting of dextran sulfate and a salt of a divalent metal ion, such as $Ca^{2+}$ and $Mg^{2+}$, preferably magnesium chloride ($MgCl_2$); terephthalate (PTA) and a divalent metal ion, such as $Ca^{2+}$ and $Mg^{2+}$, preferably magnesium chloride ($MgCl_2$); and polyethylene glycol (PEG) 6000, dextran sulfate 50,000, sodium chloride (NaCl) and a salt of a divalent metal ion, such as $Ca^{2+}$ and $Mg^{2+}$, preferably magnesium chloride ($MgCl_2$). In one embodiment the precipitation agent is dextran sulfate 50,000 and $MgCl_2$. With this precipitation agent, HDL lipoprotein will remain in free form within the plasma sample while LDL and VLDL lipoprotein will become complex bound and precipitate within the plasma fraction present in the first capillary cavity 124 of the second pathway 120.

In the first capillary cavity 114 of the first pathway 110 a buffer agent selected from the group consisting of buffer agents providing a pH within the range of 8-10, and preferably the buffer agent is tris(hydroxymethyl)-aminomethane (TRIS).

In the first capillary cavity 134 of the third pathway 130 a buffer agent selected from the group consisting of a buffer agent providing a pH within the range of 10-11 is provided. Preferably the buffer agent is glycine. Further, in the first capillary cavity 134 also one enzyme chosen from the group consisting of lipase and glycerol dehydrogenase (GYDH) is provided, preferably GYDH is provided in the first capillary cavity.

In the first capillary cavity 144 of the fourth pathway 140 glucose dehydrogenase (GDH), optionally mutarotase, a coenzyme β-nicotinamide adenine dinucleotide sodium salt ($NAD^+$) and diaphorase is provided together with a chromophore, preferably a redox indicator dye, such as 3-(4,5-dimethylthiazole-2-1)-2,5-diphenyl-2H-tetrazolium bromide (MTT).

The reactions taking place within the first capillary cavity 144 of the fourth pathway 140 are the following (enzymes for the different reactions are given within parentheses after each reaction):

Glucose+$NAD^+$→gluconolactone+NADH+$H^+$(GDH)  1)

MTT+NADH+$H^+$→formazan+$NAD^+$(diaphorase)  2)

The amount of formed formazan is in direct correlation with the amount of glucose in the body fluid sample.

In each pathway respective first capillary cavity 114, 124, 134, and 144 is in communication with a respective second centrifugation cavity 115, 125, 135, and 145. A capillary lock is provided between respective first capillary cavity 114, 124, 134, and 144 and respective second centrifugation cavity 115, 125, 135, and 145. Thus, the plasma fraction sample may only enter into the second centrifugation cavity 115, 125, 135, and 145 by subjecting the sample acquiring device to a second centrifugation. Thus, the plasma fraction sample with a buffer in the first capillary cavity 114 in the first pathway 110 enters the second centrifugation cavity 115 when being subjected to a second centrifugation, the plasma fraction sample with precipitated LDL and VLDL lipoproteins and free HDL in the first capillary cavity 124 in the second pathway 120 enters the second centrifugation cavity 125 when being subjected to a second centrifugation, the plasma fraction sample with buffer and an enzyme, preferably GYDH in the first capillary cavity 134 in the third pathway 130 enters the second centrifugation cavity 135 when being subjected to a second centrifugation and the plasma fraction sample with reagents in the first capillary cavity 144 in the fourth pathway 140 enters the second centrifugation cavity 145 when being subjected to a second centrifugation.

In this embodiment the capillary lock between the first capillary cavity and the second centrifugation cavity is provided by having an increased distance between the surfaces forming the pathway in a borderline between the first capillary cavity and the second centrifugation cavity.

After a sufficient time of centrifugation the rotation is again stopped or decreased to remove or decrease the centrifugal force acting on the plasma fraction samples in the sample acquiring device within each second centrifugation cavity 115, 125, 135, and 145.

Respective second centrifugation cavity 115, 125, 135, 145 of each pathway 110, 120, 130 and 140 is in capillary communication with a respective second capillary cavity 116, 126, 136, and 146, such that at least a fraction of the plasma fraction sample present in the second centrifugation cavity 115, 125, 135, and 145 may be transferred from said second centrifugation cavity to said second capillary cavity 116, 126, 136, and 146. In the shown embodiment in FIG. 5B, the second centrifugation cavities 115, 125, 135, 145 also have a lower portion and an upper portion oriented relative each other such that a centrifugation of the sample acquiring device will force any sample in the second centrifugation cavities towards the lower portion thereof. In the second pathway, the precipitated LDL and VLDL lipoproteins will gather in the lower part of the second centrifugation cavity 125 of the second pathway 120 during the centrifugation, while the plasma fraction containing free HDL will be positioned in the upper part of the second centrifugation cavity 125. The respective second capillary cavity 116, 126, 136, 146 of each pathway 110, 120, 130, 140 is only in capillary communication with the upper portion of the respective second centrifugation cavity of each pathway. Thus, it is only a small fraction of the plasma fraction sample which will be transferred into the second capillary cavity of each pathway, and especially in the second pathway, the precipitated LDL and VLDL lipoproteins will not be transferred into the second capillary cavity 126 of the second pathway 120.

In the second capillary cavity 126 of the second pathway 120 cholesterol esterase (CE); cholesterol dehydrogenase (CDH), a coenzyme β-nicotinamide adenine dinucleotide sodium salt ($NAD^+$) and diaphorase is provided together with a chromophore, preferably a redox indicator dye, such as 3-(4,5-dimethylthiazole-2-1)-2,5-diphenyl-2H-tetrazolium bromide (MTT).

The reactions taking place within the second capillary cavity 126 of the second pathway 120 are the following (enzymes for the different reactions are given within parentheses after each reaction):

HDL cholesterol esters+$H_2O$→HDL cholesterol+ RCOOH (CE)  1)

HDL cholesterol+$NAD^+$→HDL-Cholest-4-en-3-one+ NADH+$H^+$(CDH)  2)

MTT+NADH+$H^+$→formazan+$NAD^+$(diaphorase)  3)

The amount of formed formazan is in direct correlation with the amount of HDL in the body fluid sample.

In the second capillary cavity 116 of the first pathway 110 also cholesterol esterase (CE); cholesterol dehydrogenase (CDH), a coenzyme β-nicotinamide adenine dinucleotide sodium salt ($NAD^+$) and diaphorase is provided together with a chromophore, preferably a redox indicator dye, such as 3-(4,5-dimethylthiazole-2-1)-2,5-diphenyl-2H-tetrazolium bromide (MTT).

The reactions taking place within the second capillary cavity 116 of the first pathway 110 are the following (enzymes for the different reactions are given within parentheses after each reaction):

Cholesterol esters+$H_2O$→Cholesterol+RCOOH (CE)  1)

Cholesterol+$NAD^+$→Cholest-4-en-3-one+NADH+$H^+$ (CDH)  2)

MTT+NADH+$H^+$→formazan+$NAD^+$(diaphorase)  3)

Thus, the reactions are similar to the reactions in the second pathway with the exception that the amount of formed formazan is in direct correlation with the amount of total cholesterol (TC) in the body fluid sample.

In the second capillary cavity 136 of the third pathway 130 lipase is provided together with coenzyme β-nicotinamide adenine dinucleotide sodium salt (NAD⁺), diaphorase and a chromophore, preferably a redox indicator dye, such as 3-(4, 5-dimethylthiazole-2-1)-2,5-diphenyl-2H-tetrazolium bromide (MTT).

The reactions taking place within the second capillary cavity 136 of the third pathway 130 are the following (enzymes for the different reactions are given within parentheses after each reaction).

The formed formazan is in direct correlation with the amount of triglyceride in the body fluid sample.

Respective second capillary cavity 116, 126, 136, 146 is in communication with a respective transfer cavity 117, 127, 137 and 147 such that spontaneous flow from the capillary cavity 116, 126, 136 and 146 is prevented. Also here a capillary lock is provided in the borderline between the second capillary cavity 116, 126, 136, 146 and the transfer cavity 117, 127, 137, 147. Thus, the plasma fractions containing the reagents may only enter into the transfer cavity 117, 127, 137 and 147 by subjecting the sample acquiring device to a third centrifugation. Thus, the plasma fraction containing the reagents in the second capillary cavity 116 in the first pathway 110 enters the transfer cavity 117 when being subjected to a third centrifugation, the plasma fraction containing the reagents in the second capillary cavity 126 in the second pathway 120 enters the transfer cavity 127 when being subjected to a third centrifugation, the plasma fraction containing the reagents in the second capillary cavity 136 in the third pathway 130 enters the transfer cavity 137 when being subjected to a third centrifugation, and the plasma fraction containing the reagents in the second capillary cavity 146 in the fourth pathway 140 enters the transfer cavity 147 when being subjected to a third centrifugation.

In this embodiment the capillary lock between the second capillary cavity and the transfer cavity is provided by having an increased distance between the surfaces forming the pathway in a borderline between the second capillary cavity and the transfer cavity.

From respective transfer cavity 117, 127, 137 and 147, the plasma fraction containing the reagents further enters the first measurement cavity 111, second measurement cavity 121, third measurement cavity 131 and fourth measurement cavity 141, respectively. Thus, the plasma fraction in transfer cavity 117 enters the first measurement cavity 111, the plasma fraction in the transfer cavity 127 enters the second measurement cavity 121, the plasma fraction in the transfer cavity 37 enters the third measurement cavity 31, and the plasma fraction in the transfer cavity 147 enters the fourth measurement cavity 141.

After a sufficient time of centrifugation the rotation is decreased to decrease the centrifugal force acting on the plasma fraction samples in the measurement cavities 111, 121, 131 and 141, and spectrophotometric measurements are performed on the plasma fractions within the measurement cavities 111, 121, 131 and 141.

In one embodiment of the sample acquiring device, according to FIGS. 5A and 5B, some cavity surfaces are covered with a surfactant/wetting agent to lower the surface tension of the cavity surfaces. With such a surfactant/wetting agent the capillary forces are enhanced in comparison with a surface not covered with surfactant/wetting agent. In one embodiment of the sample acquiring device, at least one wall of each capillary cavity is covered with a surfactant/wetting agent. A surfactant/wetting agent also has influence on the distribution of reagents when being applied to the surfaces during manufacturing of the sample acquiring device, such reagents being buffers, enzymes, coenzymes and chromophores.

In one embodiment of the sample acquiring device, the distance between the surfaces forming the second measurement cavity is larger than the distance between the surfaces forming the first measurement cavity.

In one embodiment of the sample acquiring device, the distance between the surfaces forming the second measurement cavity is the same as the distance between the surfaces forming the first measurement cavity.

In one embodiment of the sample acquiring device, the distance between the surfaces forming the first measurement cavity is smaller than the distance between the surfaces forming the second and third measurement cavity, respectively.

In one embodiment of the sample acquiring device, the distance between the surfaces forming the first measurement cavity is smaller than the distance between the surfaces forming the second, third and fourth measurement cavity, respectively.

The sample acquiring device is adapted to be placed in a cuvette receiving cavity located off centre on a rotatable disc in the apparatus according to the invention. The rotatable disc is adapted to be rotated by an electrical motor according to a predetermined cycle.

In one embodiment of the method for spectrophotometric measurements the sample acquiring device is inserted into the cuvette receiving cavity of the rotatable disc.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

The invention claimed is:
1. A sample acquiring device comprising:
at least one inlet for receiving a body fluid sample,
at least one capillary sample reception cavity in capillary communication with said at least one inlet,
a first pathway in communication with said at least one inlet and a first measurement cavity, and
a second pathway in communication with said at least one inlet and a second measurement cavity, the second measurement cavity being separate from said first measurement cavity,
wherein the first pathway and the second pathway are in communication with said at least one capillary sample reception cavity such that spontaneous flow from the capillary sample reception cavity is prevented and such that body fluid sample is forcible from the capillary sample reception cavity into a first centrifugation cavity of said first pathway and a first centrifugation cavity of said second pathway by subjecting the sample acquiring device to a first centrifugation,
wherein said first centrifugation cavity of said first pathway is in capillary communication with a first capillary cavity of said first pathway and said first centrifugation cavity of said second pathway is in capillary communication with a first capillary cavity of said second pathway, such that at least a fraction of said body fluid sample in said first centrifugation cavity is transferable from said first centrifugation cavities to said first capillary cavities, wherein, each of the first centrifugation cavities of the first pathway and of the second pathway has a lower portion and an upper portion oriented relative each other such that centrifugation of the sample acquiring device forces any sample in the first centrifugation cavity towards the lower portion, wherein the first capillary cavity of the first pathway is in capillary communication only with the upper portion of the first centrifugation cavity of the first pathway, wherein the first capillary cavity of the second pathway is in capillary communication only with the upper portion of the first centrifugation cavity of the second pathway, wherein a precipitation agent is provided in said first capillary cavity of said second pathway, wherein said first capillary cavity of said first pathway is in communication with a second centrifugation cavity of said first pathway and said first capillary cavity of said second pathway is in communication with a second centrifugation cavity of said second pathway, such that spontaneous flow from said first capillary cavities is prevented and such that said at least a fraction of said body fluid sample from the first capillary cavities is forcible from the said first capillary cavity of said first pathway and into a second centrifugation cavity of said first pathway and from said first capillary cavity of said second pathway to a second centrifugation cavity of said second pathway by subjecting the sample acquiring device to a second centrifugation, wherein said second centrifugation cavity of said first pathway is in capillary communication with a second capillary cavity of said first pathway and said second centrifugation cavity of said second pathway is in capillary communication with a second capillary cavity of said second pathway, such that at least a fraction of said body fluid sample in said second centrifugation cavities is transferable from said second centrifugation cavities to said second capillary cavities, wherein said second capillary cavity of said first pathway is in communication with a transfer cavity of said first pathway and said second capillary cavity of said second pathway is in communication with a transfer cavity of said second pathway, such that spontaneous flow from said second capillary cavities is prevented and such that at least a fraction of said body fluid sample in said second capillary cavities is forcible from said second capillary cavity of said first pathway into said first measurement cavity via said transfer cavity of said first pathway and from said second capillary cavity of said second pathway into said second measurement cavity via said transfer cavity of said second pathway by subjecting the sample acquiring device to a third centrifugation, wherein at least one chromophore is provided in said second capillary cavity, in said transfer cavity or in said first measurement cavity of said first pathway, and wherein at least one chromophore is provided in said second capillary cavity, in said transfer cavity or in said second measurement cavity of said second pathway.

2. A sample acquiring device according to claim 1, wherein said precipitation agent comprises non-HDL lipoprotein complexing agents, preferably selected from the group consisting of dextran sulfate and a salt of a divalent metal ion, chosen from Ca2+ and Mg2+, preferably magnesium chloride (MgCl2); terephthalate (PTA) and a divalent metal ion, such as Ca2+ and Mg2+, preferably magnesium chloride (MgCl2); and polyethylene glycol (PEG) 6000, dextran sulfate 50,000, sodium chloride (NaCl) and a salt of a divalent metal ion, chosen from Ca2+ and Mg2+, preferably magnesium chloride (MgCl2).

3. A sample acquiring device according to claim 1, wherein cholesterol esterase (CE); cholesterol dehydrogenase (CDH); at least one coenzyme selected from the group consisting of β-nicotinamide adenine dinucleotide sodium salt (NAD+), NADP, thio-NAD+, thio-NADP, nicotinamide-purine dinucleotide, nicotinamide-methylpurine dinucleotide and nicotinamide-2-chloro-methylpurine dinucleotide; and at least one substance selected from the group consisting of diaphorase, phenazine methosulfate, phenazine ethosulfate, phenazine phenosulfate and Meldola blue; are provided in one or more of said second capillary cavity, said transfer cavity and said second measurement cavity of said second pathway.

4. A sample acquiring device according to claim 1, wherein cholesterol esterase (CE); cholesterol dehydrogenase (CDH); at least one coenzyme selected from the group consisting of β-nicotinamide adenine dinucleotide sodium salt (NAD+), NADP, thio-NAD+, thio-NADP, nicotinamide-purine dinucleotide, nicotinamide-methylpurine dinucleotide and nicotinamide-2-chloro-methylpurine dinucleotide; and at least one substance selected from the group consisting of diaphorase, phenazine methosulfate, phenazine ethosulfate, phenazine phenosulfate and Meldola blue; are provided in said second capillary cavity of said second pathway.

5. A sample acquiring device according to claim 1, wherein said chromophore of said first pathway and said chromophore of said second pathway are redox indicator dyes.

6. A sample acquiring device according to claim 1, wherein a buffer agent is provided in said first capillary cavity of said first pathway.

7. A sample acquiring device according to claim 6, wherein the buffer agent is selected from the group consisting of buffer agents providing a pH within the range of 8-11 preferably from the group consisting of tris(hydroxymethyl)aminomethane (TRIS), glycine and potassium phosphate.

8. A sample acquiring device according to claim 7, wherein the buffer agent is selected from the group consisting of buffer agents providing a pH within the range of 10-11, and preferably the buffer agent is glycine.

9. A sample acquiring device according to claim 1,
wherein lipase; glycerol dehydrogenase (GYDH); at least one coenzyme selected from the group consisting of β-nicotinamide adenine dinucleotide sodium salt (NAD+), NADP, thio-NAD+, thio-NADP, nicotinamide-purine dinucleotide, nicotinamide-methylpurine dinucleotide and nicotinamide-2-chloro-methylpurine dinucleotide; and at least one substance selected from the group consisting of diaphorase, phenazine methosulfate, phenazine ethosulfate, phenazine phenosulfate and Meldola blue; are provided in one or more cavities of said first pathway, wherein said one or more cavities is selected from the group consisting of said first capillary cavity, said second centrifugation cavity, said second capillary cavity, said transfer cavity, and said first measurement cavity of said first pathway, and wherein lipase and GYDH are provided in separate cavities.

10. A sample acquiring device according to claim 9, wherein said one or more cavities is selected from the group consisting of said first capillary cavity and said second capillary cavity of said first pathway.

11. A sample acquiring device according to claim 7, wherein the buffer agent is selected from the group consisting of buffer agents providing a pH within the range of 8-10, and preferably the buffer agent is tris(hydroxymethyl)aminomethane (TRIS).

12. A sample acquiring device according to claim 1, wherein cholesterol esterase (CE); cholesterol dehydrogenase (CDH); at least one coenzyme selected from the group consisting of β-nicotinamide adenine dinucleotide sodium salt (NAD+), NADP, thio-NAD+, thio-NADP, nicotinamide-purine dinucleotide, nicotinamide-methylpurine dinucleotide and nicotinamide-2-chloro-methylpurine dinucleotide; and at least one substance selected from the group consisting of diaphorase, phenazine methosulfate, phenazine ethosulfate, phenazine phenosulfate and Meldola blue; are provided in one or more of cavities of said first pathway, and wherein said one or more cavities is selected from the group consisting of said first capillary cavity, said second centrifugation cavity, said second capillary cavity, said transfer cavity, and said first measurement cavity of said first pathway.

13. A sample acquiring device according to claim 12, wherein said one or more cavities is selected from the group consisting of said first capillary cavity and said second capillary cavity of said first pathway.

14. A sample acquiring device according to claim 1,
wherein the second centrifugation cavity of the second pathway has a lower portion and an upper portion oriented relative each other such that a centrifugation of the sample acquiring device will force any sample in the second centrifugation cavity towards the lower portion, and
wherein the second capillary cavity of the second pathway is in capillary communication only with the upper portion of the second centrifugation cavity of the second pathway.

15. A sample acquiring device according to claim 1,
wherein the second centrifugation cavity of the first pathway has a lower portion and an upper portion oriented relative each other such that a centrifugation of the sample acquiring device will force any sample in the second centrifugation cavity towards the lower portion, and
wherein the second capillary cavity of the first pathway is in capillary communication only with the upper portion of the second centrifugation cavity of the first pathway.

16. An apparatus for spectrophotometric measurements of high density lipoprotein (HDL) and at least one of total cholesterol and triglycerides,
wherein the apparatus has a rotatable disc adapted to be rotated by an electrical motor according to a predetermined cycle,
wherein the rotatable disc has a cuvette receiving cavity adapted for receiving the sample acquiring device according to claim 1, said cuvette receiving cavity being located off center on said rotatable disc, and
wherein said apparatus has optical measurement units adapted for spectrophotometric measurements of at least said first and second measurement cavity of said sample acquiring device.

17. A sample acquiring device according to claim 1, wherein the first pathway and the second pathway are discrete relative to each other.

* * * * *